United States Patent
Brestoff et al.

(10) Patent No.: US 9,754,220 B1
(45) Date of Patent: *Sep. 5, 2017

(54) USING CLASSIFIED TEXT AND DEEP LEARNING ALGORITHMS TO IDENTIFY MEDICAL RISK AND PROVIDE EARLY WARNING

(71) Applicants: Nelson E. Brestoff, Sequim, WA (US); Jonathan Brestoff Parker, St. Louis, MO (US)

(72) Inventors: Nelson E. Brestoff, Sequim, WA (US); Jonathan Brestoff Parker, St. Louis, MO (US)

(73) Assignee: INTRASPEXION INC., Sequim, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/413,335

(22) Filed: Jan. 23, 2017

Related U.S. Application Data (63) Continuation-in-part of application No. 15/277,458, filed on Sep. 27, 2016, now Pat. No. 9,552,548.

(60) Provisional application No. 62/357,803, filed on Jul. 1, 2016.

(51) Int. Cl.
| | |
|---|---|
| *G06F 15/18* | (2006.01) |
| *G06N 99/00* | (2010.01) |
| *G06F 17/28* | (2006.01) |
| *G06F 19/00* | (2011.01) |

(52) U.S. Cl.
CPC ........... *G06N 99/005* (2013.01); *G06F 17/28* (2013.01); *G06F 19/322* (2013.01); *G06F 19/3431* (2013.01)

(58) Field of Classification Search
USPC .......................................................... 706/12
See application file for complete search history.

(56) References Cited

U.S. PATENT DOCUMENTS

| | | | | |
|---|---|---|---|---|
| 8,949,170 B2 * | 2/2015 | Zadeh | ...................... | G06N 7/02 |
| | | | | 706/48 |
| 9,063,930 B2 * | 6/2015 | Zadeh | ...................... | G06N 7/02 |
| 9,171,261 B1 * | 10/2015 | Zadeh | ...................... | G06N 7/02 |
| 9,202,253 B2 * | 12/2015 | Macoviak | ............. | G06F 19/328 |
| 9,224,180 B2 * | 12/2015 | Macoviak | ............. | G06F 19/328 |
| 9,262,688 B1 * | 2/2016 | Zadeh | ...................... | G06N 7/02 |

(Continued)

OTHER PUBLICATIONS

ConfidentCare: A Clinical Decision Support System for Personalized Breast Cancer Screening Ahmed M. Alaa; Kyeong H. Moon; William Hsu; Mihaela van der Schaar IEEE Transactions on Multimedia Year: 2016, vol. 18, Issue: 10 pp. 1942-1955, DOI: 10.1109/TMM.2016.2589160 IEEE Journals & Magazines.*

(Continued)

*Primary Examiner* — Michael B Holmes
(74) *Attorney, Agent, or Firm* — Cotman IP Law Group, PLC (57) ABSTRACT

Deep learning is used to identify specific, potential risks of missed diagnosis for a patient and reporting the risk to healthcare provider. The system involves mining and using existing electronic health records for specific medical diagnosis to train one or more deep learning algorithms, and then examining the internal electronic health record of the patient with the trained algorithm, to generate a scored output that will enable a healthcare provider to be alerted to potential risks of a missed diagnosis.

11 Claims, 5 Drawing Sheets

(56) References Cited

U.S. PATENT DOCUMENTS

| | | | |
|---|---|---|---|
| 9,324,022 | B2 | 4/2016 | Williams, Jr. et al. |
| 9,424,533 | B1* | 8/2016 | Zadeh .................. G06N 7/02 |
| 9,552,548 | B1* | 1/2017 | Brestoff ................ G06N 3/08 |
| 2004/0024775 | A1 | 2/2004 | Kemp |
| 2004/0205661 | A1 | 10/2004 | Gallemore |
| 2010/0325171 | A1 | 12/2010 | Lopez |
| 2013/0297519 | A1 | 11/2013 | Brestoff et al. |
| 2014/0244524 | A1 | 8/2014 | Brestoff et al. |
| 2015/0370979 | A1 | 12/2015 | Boloor et al. |

OTHER PUBLICATIONS

System Light-Loading Technology for mHealth: Manifold-Learning-Based Medical Data Cleansing and Clinical Trials in We-Care Project Anpeng Huang; Wenyao Xu; Zhinan Li; Linzhen Xie; Majid Sarrafzadeh; Xiaoming Li; Jason Cong IEEE Journal of Biomedical and Health Informatics Year: 2014, vol. 18, Issue: 5 pp. 1581-1589, IEEE Journals & Magazines.*

Secure and Connected Telehealth Approach to Mitigating Concussion Risks in Student Athletes Matthew Morrison; George Humphrey; John Daigle; John Ralston; Jason Thibado; Andreas Ralston 2016 25th International Conference on Computer Communication and Networks (ICCCN) Year: 2016 pp. 1-9, DOI: 10.1109/ICCCN.2016.7568570 IEEE.*

An Automatic Electronic Nursing Records Analysis System Based on the Text Classification and Machine Learning Zhang Wei; Zheng Xian Ju; Xie Chun; Jiang Hua; Peng Jin 2013 5th International Conference on Intelligent Human-Machine Systems and Cybernetics Year: 2013, vol. 2 pp. 494-498, DOI: 10.1109/IHMSC.2013.265 IEEE Conference Publications.*

Barclift, Z.J. 2008. "Preventive Law: A Strategy for Internal Corporate Lawyers to Advise Managers of Their Ethical Obligations." Journal of the Legal Profession 33, p. 31 (2008).

Borden, Bennett P. and Baron, Jason R. 2014. "Finding the Signal in the Noise: Information Governance, Analytics, and the Future of Legal Practice," 20 Rich J. L. & Teck 7, 20 and 29-30.

Brestoff, N. 2012. "Data Lawyers and Preventive Law," Law Technology News.

Brown, Louis M., "Lawyering Through Life: The Origin of Preventive Law," (1984).

Miotto, R., et al. "Deep Patient: An Unsupervised Representation to Predict the Future of Patients from the Electronic Health Records." Sci. Rep. 6, 26094; doi: 10.1038/srep 26094 (2016).

Choi, E., et al., "Doctor AI: Predicting Clinical Events via Recurrent Neural Networks, Proceedings of Machine Learning for Healthcare." arXiv: 1511.05942v11 [cs.LG] Sep. 28, 2016.

Lipton, Z, et al., "Learning to Diagnose with LSTM Recurrent Neural Networks," a conference paper at ICLR 2016. arXiv: 1511.03677v6 [cs.LG] Mar. 1, 2016.

Cheng, Yu, et al., "Risk Prediction with Electronic Health Records: A Deep Learning Approach".

Choi, E., et al., "Using recurrent neural network models for early detection of heart failure onset," J. Am. Med. Inform. Assoc. 2016; 0:1-9; doi: 10.1093/jamia/ocw112, Research and Applications.

* cited by examiner

FIGURE 5

USING CLASSIFIED TEXT AND DEEP LEARNING ALGORITHMS TO IDENTIFY MEDICAL RISK AND PROVIDE EARLY WARNING

CROSS-REFERENCE TO RELATED APPLICATIONS

The present application is a Continuation-In-Part of U.S. patent application Ser. No. 15/277,458, filed on Sep. 27, 2016, which claims the benefit of U.S. Provisional Application Ser. No. 62/357,803, filed on Jul. 1, 2016, all of which are herein incorporated by reference for completeness of disclosure.

BACKGROUND OF THE INVENTION

Field of the Invention

This invention relates generally to machine learning and more specifically to training deep learning algorithms as text classifiers and using them to identify risks while they are still internal to the enterprise, including the risks of potential litigation.

Description of the Related Art

Law professor Louis M. Brown (1909-1996) advocated "preventive law." Indeed, he pioneered this concept. His philosophy was this: "The time to see an attorney is when you're legally healthy—certainly before the advent of litigation, and prior to the time legal trouble occurs." He likened his approach to preventive medicine. However, Prof. Brown passed away before computer hardware and software had reached the point where his concept could be implemented. There are no conferences or journals today which focus on preventive law.

In modern society, entities such as commercial businesses, not-for-profit organizations, governmental agencies, and other ongoing concerns (all hereinafter referred to collectively as "enterprises") are exposed to potential liabilities if they breach contractual, criminal, governmental, or tort obligations.

In *Preventing Litigation: An Early Warning System, Etc.* (Business Expert Press 2015) ("*Preventing Litigation*"), I presented the data showing that the average annual cost of commercial tort litigation in terms of payouts, defense attorneys' fees, and administrative expenses (collectively, "cost"), during the 10-year period from 2001 through 2010, was $160 billion. The total cost for that 10-year timeframe was $1.6 trillion. That pain is enormous.

In *Preventing Litigation*, I compiled the federal and state caseload for that same 10-year period, and computed the cost per case. The result was $408,000, but I concluded that the cost per case was better set at $350,000, as a minimum.

Since litigation is neither a cost of goods sold nor a cost of services provided, this result indicates a loss to the enterprise of net gains of over $1 million for only three average commercial tort litigation matters, but it was not surprising. It is common knowledge that the cost of litigation is high. On occasion, employee misbehavior, at every level, has violated the rights of another employee, severely impaired an enterprise, harmed an entire marketplace, or physically harmed enterprise employees, members of the public, or violated their rights. However, I assert that my data compilation and calculation was the first "per case" derivation of the average cost per case. I showed how much of a losing proposition it is for an enterprise to have to defend a commercial tort litigation matter, even if the client's attorneys are successful in the defense they mount.

Worse, severe misconduct causing massive financial and/or physical harm may escalate to the level where criminal charges are filed. Such charges may be filed against the enterprise and the individuals responsible for the harm. In the early 1990s, the Federal Sentencing Guidelines provided benchmarks for misconduct. The Sentencing Guidelines make room for mitigating conduct and actions that speak against the heaviest penalties. In this context, a system enabling the prevention of harm may function to avoid criminal prosecution altogether. Such a system is evidence of a specific intent to avoid harm, which is the opposite of an element any prosecutor would be forced by law to meet: a specific intent to do harm.

However, litigation can cost an enterprise in still other ways. For example, the enterprise's reputation may suffer, productivity may be reduced, as when an executive or technology employee receives a litigation hold notice and must divert his or her attention from the matters at hand; meets with in-house or outside counsel; or prepares for and then sits for a deposition or testifies in court.

These high costs and risks are sufficient motivation to find a way to identify the risks of litigation before the damage is done. If a risk can be identified and eliminated before causing damage, the risk cannot give rise to a lawsuit. No civil lawsuit is viable without a good faith allegation of the necessary element of damages.

The attorneys who are closest to the data internal to an enterprise are the attorneys employed by the enterprise. However, these in-house attorneys are blind to the data which contain indications of litigation risks.

There is no software technology or product extant today which permits enterprise employees to identify and surface examples of the risks of being sued while they are still only potential legal liabilities.

Thus, there is a need for a system capable of identifying an enterprise's own internal risks, including but not limited to the risk of litigation, and providing early warning to appropriate personnel.

BRIEF SUMMARY OF THE INVENTION

This invention comprises a computer-enabled software system using deep learning to identify specific, potential risks of litigation while such risks are still "internal electronic communications" ("IECs"); that is, while the internal communications are contained on company computer resources, and are subject to monitoring by the company based on policies and notifications. IECs may be emails and any attachments thereto, a collection of call center notes, a set of warranty claims, other text documents, or transcriptions of voice mail messages. For simplicity we refer to all IECs as either emails (including attachments) or as "test" data. One or more embodiments of the invention relies on existing classifications of litigation data to train one or more deep learning algorithms, and then to examine IECs with them, to generate a scored output that will enable enterprise personnel, most likely attorneys or other legal department personnel, to be alerted to risks while they are still only potential lawsuits. A computer-based examination of IECs could be near real-time, e.g., overnight. After all, the purpose of an early warning system is to enable the enterprise to be proactive instead of reactive, and as soon as possible.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

The present invention comprising using classified text and deep learning algorithms to identify risk and provide early warning will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art would recognize that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. It should be noted that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item. The terms "email" and "Email" both refer to an email and any attachment.

The term "algorithm" refers to a "deep learning algorithm," "deep learning neural network," or a "deep learning model," all of which here refer to a form of text classification.

One or more embodiments of the present invention will now be described with references to FIGS. 1-5.

Figure 1:
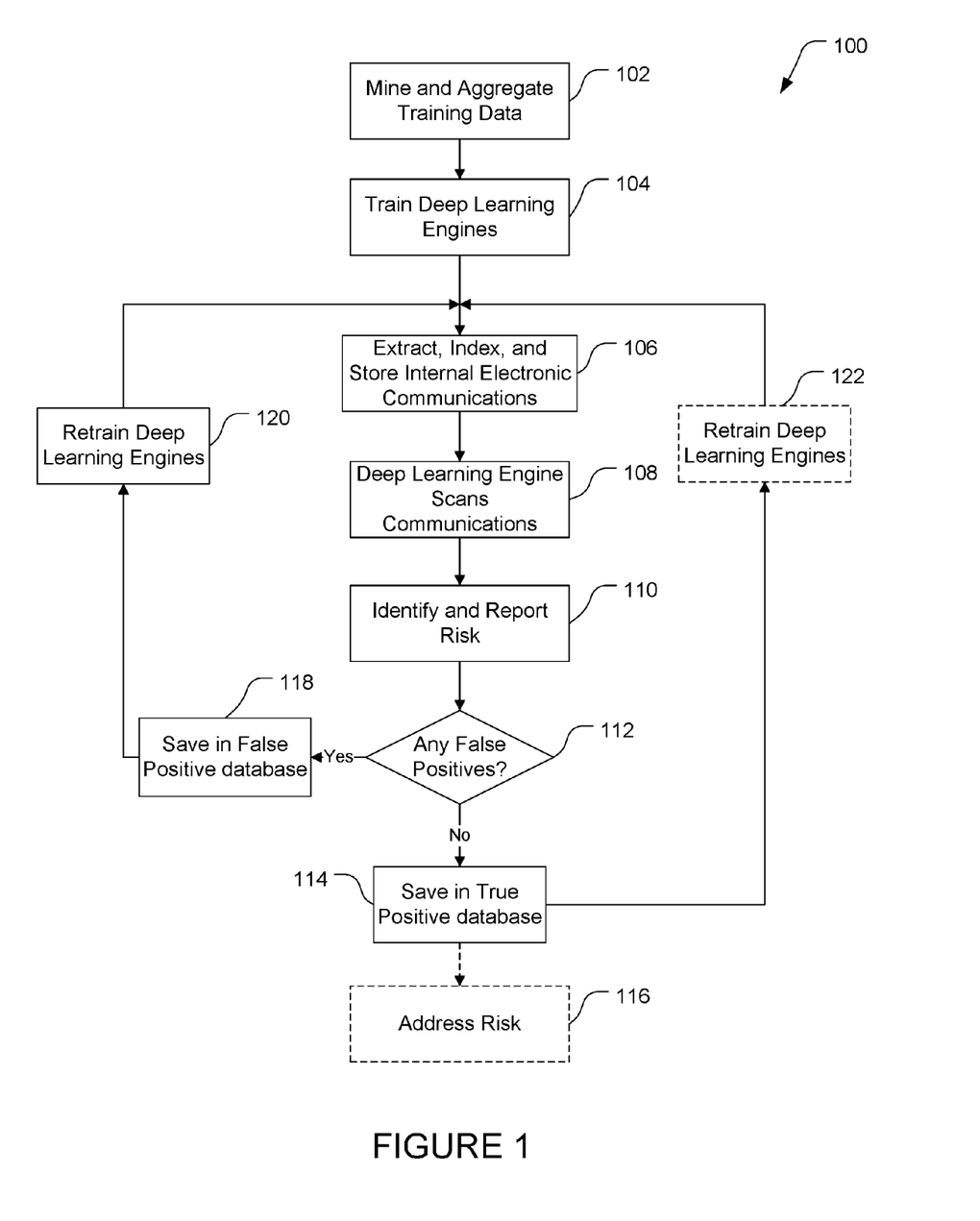
FIG. 1 is a flow chart illustration of the process for using classified text and deep learning algorithms to identify risk and provide early warning in accordance with one or more embodiments of the present invention.

FIG. 1 is a flow chart illustration of the process 100 for using classified text and deep learning algorithms to identify risk and provide early warning. As illustrated, the process 100 begins at block 102 with mining of data for training one or more deep learning algorithms. In the typical instance, subject matter experts identify one or more datasets with classifications of risk or threats having a sufficient number of textual documents. These classifications (or categories or labels) of risk are more typically from sources outside of the enterprise. The system data-mines such classified datasets to extract a sufficient number of documents within a specific category to train one or more deep learning algorithms.

In the context of litigation risk, for example, a subject matter expert would note that the federal court litigation database known as the Public Access to Court Electronic Records (PACER) is based on well over one hundred case types, to which PACER assigns Nature of Suit (NOS) codes. When a federal court lawsuit is initiated, the person filing it must complete and file a form called a Civil Cover Sheet, which instructs the person responsible for filing the lawsuit to review a list of NOS codes and choose one and only one code which best describes the lawsuit, even if there is more than one theory of recovery.

To create a set of training documents for a particular federal court litigation risk, a user of this invention would use PACER's Application Programming Interface (API) to obtain hundreds if not thousands of text documents from previous lawsuits which have been filed in a specific NOS category. Such a user would then compile a large number of training documents which describe the facts (not the law) which prompted the lawsuit to be filed in the first place.

In this illustrative example, PACER would be a generic source of classified text outside of the enterprise, which is as training data. A ready (but not the only) source of training data is a lawsuit complaint in a specific case-type category, as identified by its NOS category name or number.

NOS categories are not difficult to understand. One of them, for example, is the category of Civil Rights-Employment which, in other words, means illegal discrimination against employees, whether it is for age, race, sex, or some other subclass of illegal discrimination. In addition, and among over one hundred categories, there are codes for breach of contract, fraud and product liability case-types.

There may be other sources of training data, i.e. internal enterprise sources of specific litigation-case-type training data. Some examples are: textual data from the previous litigation history of an enterprise; text in warranty claims; and data from the confirmation by a user that a specific system output document (e.g., email) has been scored by the algorithm in a way indicating that it should be saved and used for re-training the algorithm.

Using litigation case-type data, a complaint is usually (but not always) identified as the first document in a litigation docket, i.e. Document Number 1. In order to train a deep learning algorithm, the focus is on the factual allegations in these complaints. These factual allegations may be stated in a section of a complaint entitled "Background Facts" or the like.

Many sections of a complaint are unnecessary and consist of legalistic statements that can be deleted for the purpose of training the algorithm. For example, the sections that pertain to jurisdiction, venue, the identification of the parties, the legal theories for recovery, and the prayer for damages are unnecessary. By deleting unnecessary text, the amount of training data is reduced, and the training data will contain less "noise" for analysis by the deep learning algorithm.

In some cases, the plaintiff in a case may be represented by an attorney. In that case, the fact section is based on information provided by the attorney's client and by the information stemming from the attorney's research. Because attorneys typically present facts in a logical way, so as to be both understood and persuasive, we assume that such facts have been vetted. For this reason, complaints written by counsel are a prime source of training data.

However, additional facts may be developed after the complaint is filed and during the discovery of electronically stored information, e.g., by way of production of documents, responses to written interrogatories, or by testimony given during depositions and the like. Although such facts are generally not placed in the public record, certain key facts are put into the public record (e.g. in PACER) as part of motions for summary judgment.

The data mining needed to create a strong deep learning algorithm aims at surfacing a large number of factual allegations within a specific risk case-type.

In one or more embodiments, the system's primary, but not only, source of training data consists of the facts alleged in previously filed complaints filed in a specific category of lawsuit.

Such litigation data is positive training data, and typically contains no emails. The risks the system of the present invention would seek to surface test data that would be "related" to the aggregation of these positive facts. The degree of the relation is reported by an accuracy score ranging from 0.50 to a maximum of 1.0. The training data also includes negative training data, such as text concerning some unrelated topic, e.g., the Holy Roman Empire. (Negative, unrelated training data may be obtained from Wikipedia, for example.) The system uses negative training data to better score test data as either related or unrelated to a specific case-type.

The training data is crucial for a deep learning engine to be able to produce an accuracy score for the text in the test data, which typically consists primarily of emails. The algorithm can produce an accuracy score by comparing an email, as encoded, to the vector space described by the positive training data related to the risk, and to the negative training data, which is unrelated.

The process of aggregating this training material and providing it to a deep learning engine involves creating a "vector" for each word in the block in relation to the two or three words before and after it. Accordingly, each word vector has its own context, and that context is meaningful in connection with the type of case (and the type of risk) for which the deep learning algorithm is being trained. Transforming the text used in a specific classification (or, for litigation, specific category or type of case) into numerical vectors may be accomplished via various methods such as Word2vec by Tomas Mikolov at Google, "GloVe: Global Vectors for Word Representation" by Jeffrey Pennington, et al., etc.

However, to make the matter clear, although the deep learning algorithm will encode the text in the above-described manner, i.e. words within the context of other words, the factual allegations are not provided to the algorithm word by word, sentence by sentence, or paragraph by paragraph. Instead, the whole block of factual allegations is presented for ingestion as a document.

One object of amassing a sufficient number (hundreds if not thousands) of training documents is to train a deep learning algorithm so that it functions well, and so is considered "strong." Consequently, at step 104, category-specific training documents are passed to, and ingested by, one or more deep learning algorithms best suited to handle natural language processing (NLP). The algorithm more commonly used in the context of NLP and text analysis, is known to practitioners in the art as a recurrent neural networks (RNN).

Such deep learning RNNs use hidden computational "nodes" and various "gates," and require manipulation known in the art as "tuning." After the process of "tuning", the algorithm will be evaluated to assess the degree to which it accurately identifies the textual test data it has never before encountered with the "vector space" it has been trained to recognize. As one example, practitioners construct a Receiver Operating Characteristic (ROC) graph and calculate the Area Under the Curve (AUC) score. An ROC graph measures true positives (on the y-axis) versus false positives (on the x-axis). Because the maximum AUC score is one (1.0), an ROC-AUC score in the mid-nineties, e.g., 0.95, indicates that there are far more true positives than false positives. In experiments, described below, the RNNs of the present invention have achieved scores above 0.967.

When an algorithm is trained to "understand" a particular type of case, it may be thought of as a "filter." Typically, the system will consist of more than one filter. The system passes the enterprise data through each filter. The reason is clear: A deep learning algorithm trained to identify "breach of contract" risks, which we now call a filter, may find no risk in the test data, but an "employment discrimination" filter may find one or more high-scoring emails in the same data.

Once the Deep Learning Engine is trained, at step 106 the system indexes and also extracts text from each Email and in any attachment. Those of skill in the art will appreciate that other implementations are contemplated. For example, it may be necessary or desirable to only extract the subject line and the unstructured text in the message field. In addition, the indexed data may be stored for a specific period of time in a database, a period which the Enterprise may designate in accordance with its data destruction policies.

In one or more embodiments, the system at step 106 may operate in a non-real-time mode by extracting existing internal email data, e.g. from the previous day's Email, and then stores the data in a database. In other embodiments, the system at step 106 may operate in real-time to intercept, index, store and extract text from internal Email data.

After indexing, extracting text, and storing the internal Email data in a database, the system passes that data to each of the category-specific algorithms at step 108, which are also referred to herein as "filters." Each filter scores the data for each Email for accuracy in comparison to how each filter was trained.

Once each Email is scored for accuracy in relation to the risks or threats by one of the filters, the score and text are output at step 110. The Emails related to a particular risk may be reported as an "early warning" alert to specific employees, for example. These employees may be a predetermined list of in-house attorneys, paralegals or other employees in the legal department.

In addition, an enterprise may configure the system to send its "early warning" alert to a list of devices owned by the enterprise where the communication of the output may be encrypted using appropriate security measures.

When a scored Email is reported to a designated enterprise employee, that employee may be enabled to review the Email in one or more of several modes, e.g., the scored text in a spreadsheet format and/or a bar graph distribution. Using the spreadsheet format, after reviewing a row of score and Email text, a user may call that Email to the fore and review it in its native state. This feature is possible because the Emails were indexed when they were copied into the system.

At step 112, when a determination is made, e.g. by a reviewer such as an attorney or paralegal, that a specific Email is, at least provisionally, a false positive (and that further investigation is not warranted), the process proceeds to step 118 where the email is stored in a False Positive database. A user interface, e.g. graphical, may be provided for the reviewer to perform the necessary designations, for example. Those of skill in the art would appreciate that the system could be configured to perform this determination step automatically, with the reviewer having a veto or override capability, for example.

However, if at step 112 a determination is made that an identified Email is a true positive, a copy of that Email may be placed in a True Positive database at step 114. When a designated number of Emails have been saved for either purpose, the positive or negative training data may be updated. In this way, the generic training data may be augmented with company-specific training data. With this additional training data, the deep learning algorithms may be re-trained in steps 120 and/or 122 to amplify the positive or negative vector spaces for each filter, and to better reflect the enterprise's experience and culture.

Email marked as true positive and placed in True Positive database at step 114 may be exported via an API to the enterprise's existing litigation or investigation case management system at step 116, if any, from which the risk may be optionally addressed. The algorithm's positive output may be limited to scores which surpass a user-specified threshold, for example.

The system of the invention we have now described has two additional advantages. The first advantage is confidentiality. If the enterprise directs its legal department to install the system and have its attorneys direct and control its operation, including any involvement by the IT department, then the attorneys using the system may invoke the attorney work-product doctrine. Then, when the system provides an output to a designated list of attorneys or other legal department personnel, such as paralegals, the enterprise may again invoke the attorney-work product doctrine when someone in the legal department decides which emails to investigate. Similarly, the work-product doctrine should apply when legal department personnel use an API to access and use whatever case or investigation management platform the enterprise uses.

In addition, when an investigation appears to warrant further action of a proactive, preventive nature, the enterprise attorneys may advise a control group executive in order to invoke the attorney-client privilege.

Thus, by installing and operating the system in the manner described above, the invention provides confidentiality to the sensitive information that is being brought to light.

The second advantage arises whenever a regulatory investigation becomes problematic. Should a governmental entity file criminal charges against the enterprise and or any of its personnel, the prosecuting authorities will have to present evidence of a specific intent to do harm. But by installing and operating the system of this invention in good faith, the enterprise and anyone so charged will have countervailing evidence of a specific intent to avoid harm.

To summarize: Once the deep learning algorithm is trained, the system has three major subsystems, enterprise data, the deep learning algorithms or filter(s), and the output data. Taken together, the system operates to identify a potentially adverse risk to the enterprise and provide early warning to a user. In the exemplary embodiments provided herein, the potentially adverse risk is the risk of a specific type of litigation but could just as well be other types of risk, including the risk of physical harm to the enterprise's customers by the enterprise's products.

Figure 2:
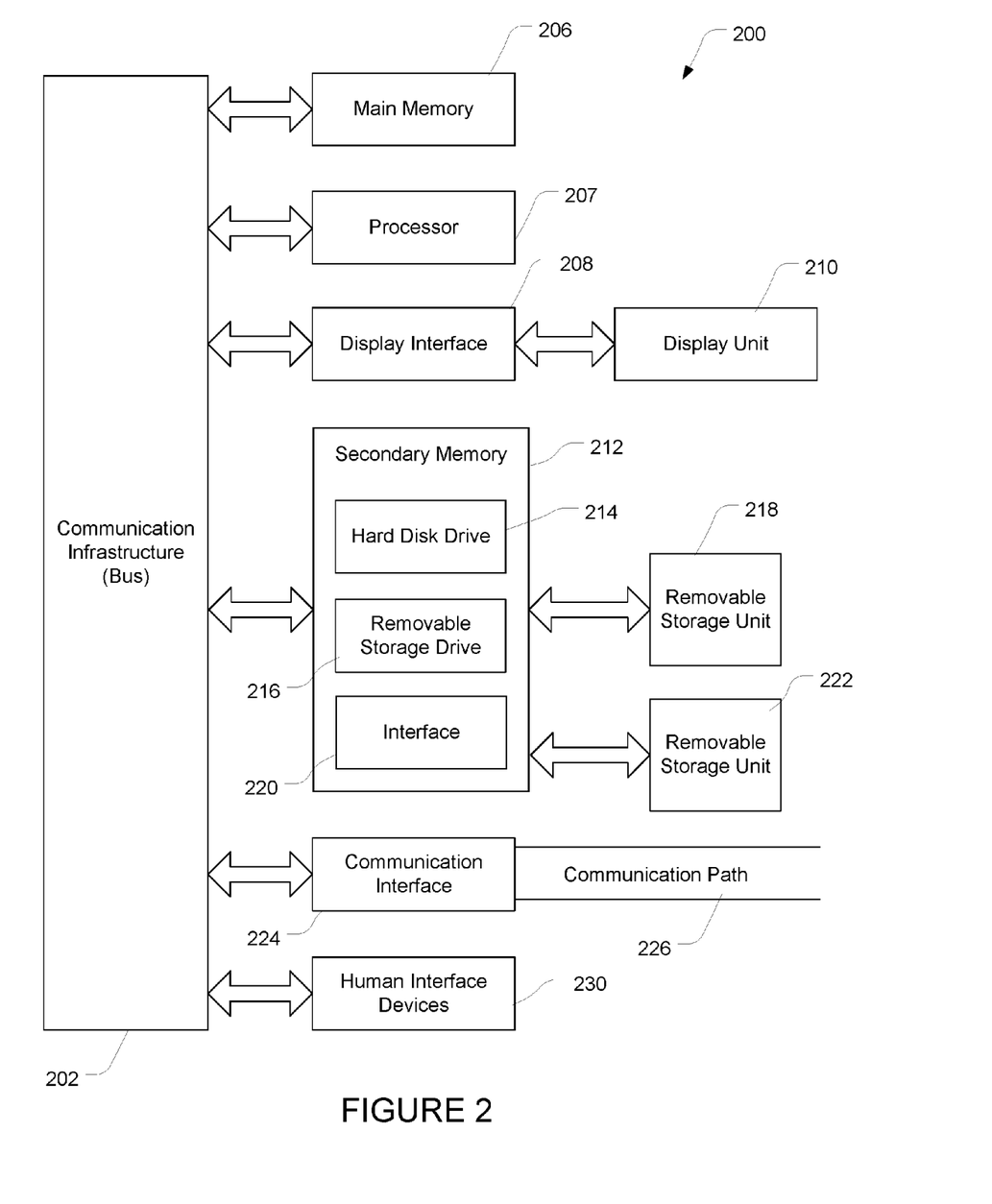
FIG. 2 illustrates a general-purpose computer and peripherals that when programmed as described herein may operate as a specially programmed computer capable of implementing one or more methods, apparatus and/or systems of the present invention.

FIG. 2 diagrams a general-purpose computer and peripherals 200, when programmed as described herein, may operate as a specially programmed computer capable of implementing one or more methods, apparatus and/or systems of the solution described in this disclosure. Processor 207 may be coupled to bi-directional communication infrastructure 202 such as communication infrastructure system bus 202. Communication infrastructure 202 may generally be a system bus that provides an interface to the other components in the general-purpose computer system such as processor 207, main memory 206, display interface 208, secondary memory 212 and/or communication interface 224.

Main memory 206 may provide a computer readable medium for accessing and executed stored data and applications. Display interface 208 may communicate with display unit 210 that may be utilized to display outputs to the user of the specially-programmed computer system. Display unit 210 may comprise one or more monitors that may visually depict aspects of the computer program to the user. Main memory 206 and display interface 208 may be coupled to communication infrastructure 202, which may serve as the interface point to secondary memory 212 and communication interface 224. Secondary memory 212 may provide additional memory resources beyond main memory 206, and may generally function as a storage location for computer programs to be executed by processor 207. Either fixed or removable computer-readable media may serve as Secondary memory 212. Secondary memory 212 may comprise, for example, hard disk 214 and removable storage drive 216 that may have an associated removable storage unit 218. There may be multiple sources of secondary memory 212 and systems implementing the solutions described in this disclosure may be configured as needed to support the data storage requirements of the user and the methods described herein. Secondary memory 212 may also comprise interface 220 that serves as an interface point to additional storage such as removable storage unit 222. Numerous types of data storage devices may serve as repositories for data utilized by the specially programmed computer system. For example, magnetic, optical or magnetic-optical storage systems, or any other available mass storage technology that provides a repository for digital information may be used.

Communication interface 224 may be coupled to communication infrastructure 202 and may serve as a conduit for data destined for or received from communication path 226. A network interface card (NIC) is an example of the type of device that once coupled to communication infrastructure 202 may provide a mechanism for transporting data to communication path 226. Computer networks such Local Area Networks (LAN), Wide Area Networks (WAN), Wireless networks, optical networks, distributed networks, the Internet or any combination thereof are some examples of the type of communication paths that may be utilized by the specially program computer system. Communication path 226 may comprise any type of telecommunication network or interconnection fabric that can transport data to and from communication interface 224.

To facilitate user interaction with the specially programmed computer system, one or more human interface devices (HID) 230 may be provided. Some examples of HIDs that enable users to input commands or data to the specially programmed computer may comprise a keyboard, mouse, touch screen devices, microphones or other audio interface devices, motion sensors or the like, as well as any other device able to accept any kind of human input and in turn communicate that input to processor 207 to trigger one or more responses from the specially programmed computer are within the scope of the system disclosed herein.

While FIG. 2 depicts a physical device, the scope of the system may also encompass a virtual device, virtual machine or simulator embodied in one or more computer programs executing on a computer or computer system and acting or providing a computer system environment compatible with the methods and processes of this disclosure. In one or more embodiments, the system may also encompass a cloud computing system or any other system where shared resources, such as hardware, applications, data, or any other resource are made available on demand over the Internet or any other network. In one or more embodiments, the system may also encompass parallel systems, multi-processor systems, multi-core processors, and/or any combination thereof. Where a virtual machine, process, device or otherwise performs substantially similarly to that of a physical computer system, such a virtual platform will also fall within the scope of disclosure provided herein, notwithstanding the description herein of a physical system such as that in FIG. 2.

Experimental Results

Embodiments of the present invention were validated using training data for the employment discrimination case-type, two similar (but different) deep learning algorithm providers, and a portion of Ken Lay's Enron email corpus. The system found one (1) risky email out of 7,665 emails.

The system as described herein requires multiple types of factual information. For example, the factual information may include but is not limited to a compilation of factual allegations previously presented as pre-litigation demands; a compilation of factual allegations previously presented as part of filed lawsuits; factual details extracted from hypothetical examples of potential legal liability as identified and preserved by authorized personnel; factual details extracted from learned treatises; factual details from employee complaints; and factual details from customer complaints.

First, text data from prior court cases (and other sources) pertaining to employment discrimination lawsuits were extracted as an example of many case-types. Second, the text data was used to train two deep learning algorithms in two ways, with documents that were related to prior employment discrimination lawsuits, and with documents that were clearly not related to an employment discrimination risk. There were no emails in the training data.

Next, as trained, the deep learning algorithms were presented with test data consisting of a portion of the Enron email subset for Ken Lay, the former Chairman and CEO of Enron. The test data consisted of only these emails.

Before the experiments, the PACER database was reviewed for statistics about Enron. For the five-year period 1997-2001, the chances of finding a workplace discrimination case against an Enron company was only about one percent (1%). During that five-year timeframe, an Enron company was named in litigation 1,339 times, and was named in an employment discrimination case only 13 times. Accordingly, there was no expectation of a significant result because it is unlikely that employees with a discrimination complaint would reach out to Ken Lay. Ken Lay was, after all, the Chairman and CEO of Enron, not a manager and not the director of Human Resources.

Next, PACER was data-mined to extract certain text portions of documents filed in the employment discrimination category to create a set of training documents in this silo.

The first experiment was with a deep learning algorithm provided by MetaMind, which was later acquired by Salesforce. The amount of training data was increased in baby steps. The first experiment used only 50 training documents, but provided immediate results, which was surprising and unexpected, in part because Ken Lay was the Chairman and CEO of Enron, not the director of the Human Resources department.

As configured for the experiment, the system reported the results in two formats. The first format is an Excel spreadsheet. There, in the first row, in Column A, the system shows the scores which indicate the accuracy of the Email text compared to the case-type for which the algorithm was trained. In Column B, the system shows a portion of the Email text associated with the score. Twenty-two (22) emails were found which scored at 0.90 or above for accuracy out of 6,352 emails, and two of them expressed a risk of employment discrimination, with one being a "forward" of the other.

Figure 3:
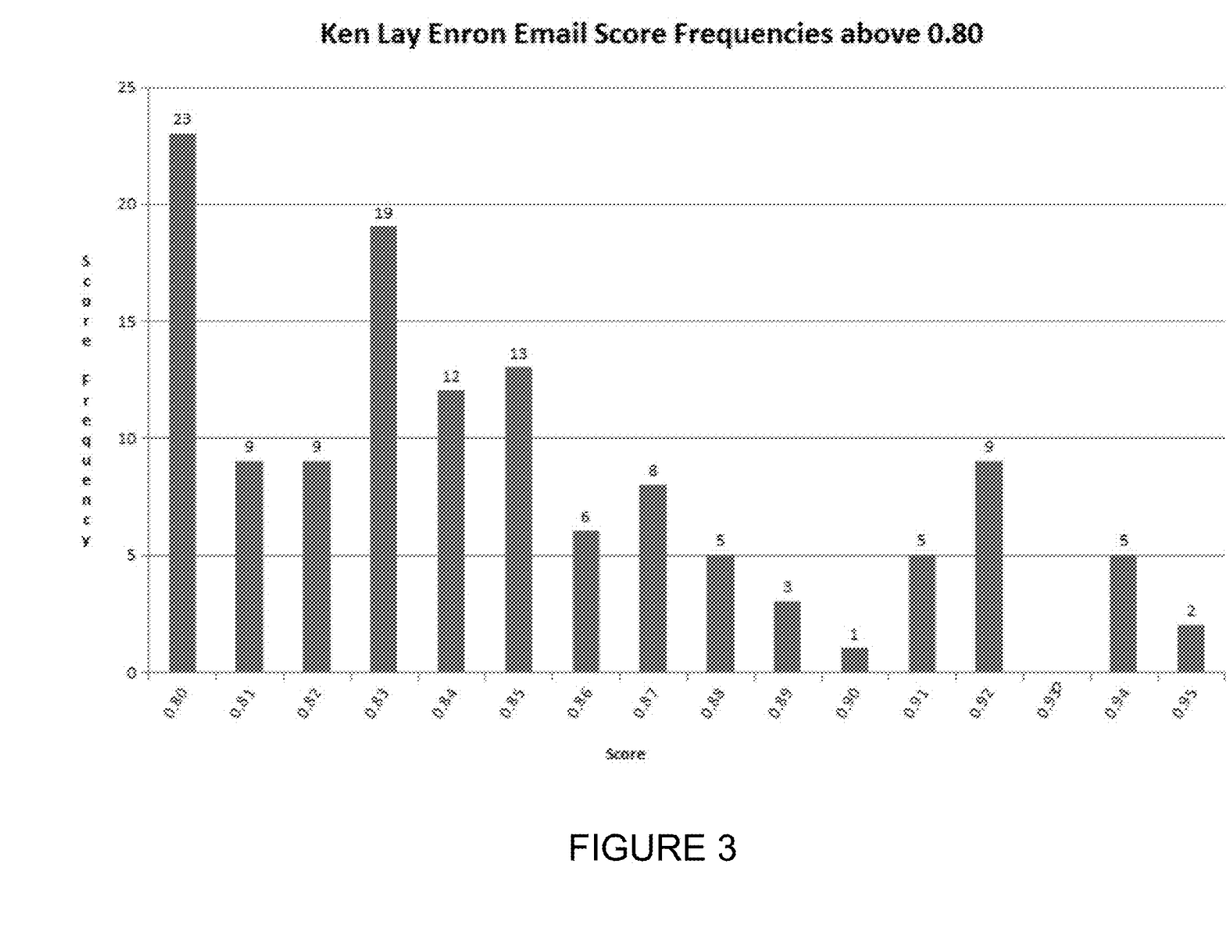
FIG. 3 is a bar graph illustration of email score frequencies above 0.80 for 400 training documents.

The second format is a bar graph of the data scored by the algorithm, illustrated in FIG. 3. The bar graph is a distribution which provides context for the highest scoring emails. On the x-axis, the bar graph shows the scores for the emails. The highest possible score is 1.0 and is on the far right. On the y-axis, the graph shows the number of emails which received any particular score. The distribution bar graph only shows the scores ranging from 0.80 to 1.00.

In reviewing the top-scoring 22 emails, i.e. the ones which scored 0.90 or above, the data showed that most of them were false positives, but two emails (as noted above) stood out. Scoring at 0.94, both of them presented a discrimination risk, but it was the same risk, because one email was a "forward" of the initial version. The subject of that email was "[M]y unfair treatment at Enron—Please HELP."

After further training, to 400 documents, the number of false positives was reduced. The deep learning algorithm scored only four (4) emails at 0.86 or higher.

In the resulting spreadsheet, lines 3 and 4 scored at the 0.86 and 0.88 levels respectively. Those emails include the phrase "my unfair treatment at Enron." Upon further review, the first paragraph of the email in the spreadsheet began: "Dear Mr. Lay, [M]y employment with Enron is to be terminated, the reason given by HR, for not meeting performance standards. However, I firmly believe that this is not the real reason, the real one being for defying the wishes of my manager . . . , who, I believe was acting in a discriminatory way towards me . . . ." (Boldface and italics added.)

As the number of our training documents increased, it became evident that the deep learning algorithm was becoming more accurate. In addition, the inclusion of a negative dataset (and vector space), e.g. pertaining to the Holy Roman Empire and calendar entries, also reduced the number of false positives in the results.

Further experiments with a list of sex and race terms demonstrated that they added little to the strength of the algorithm if anything. This may be because the lists lacked any context and were as insufficient as any list of key words.

Figure 4:
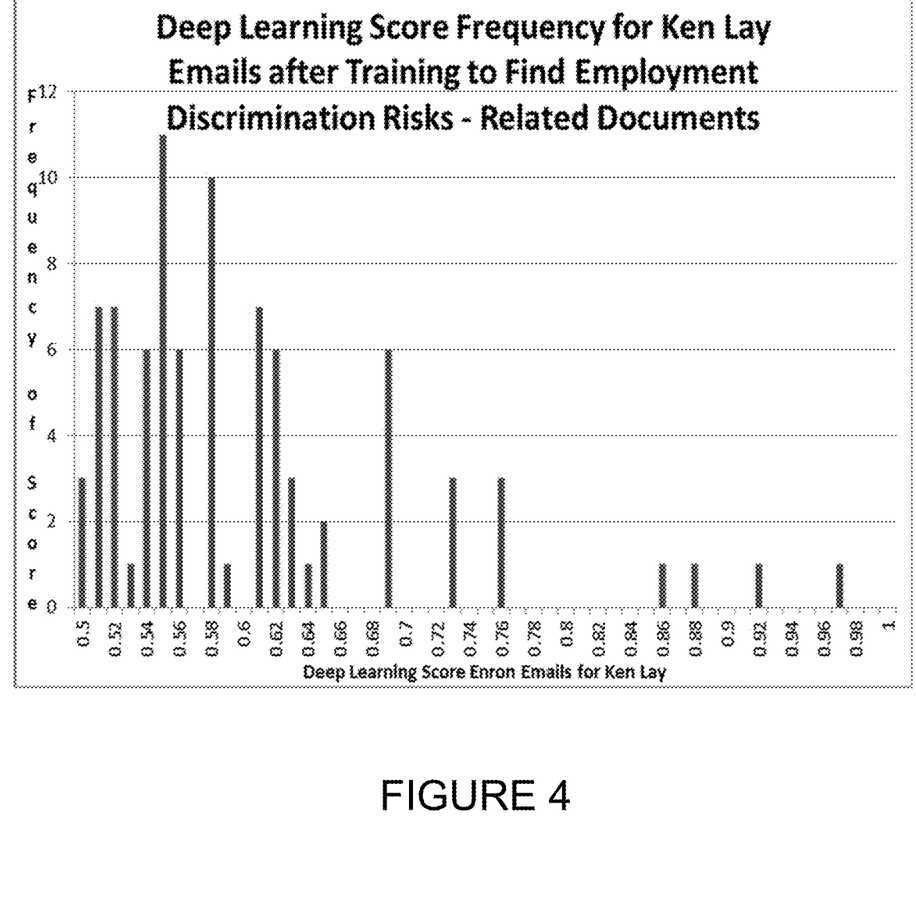
FIG. 4 is a bar graph illustration of email score frequencies after training to find employment discrimination risks.

In the experiment pertaining to the spreadsheet where four high-scoring Emails were identified, about 400 training documents were used. As previously mentioned, only four emails scored at or above 0.80 for accuracy with respect to the training data. Two emails scored above 0.90 for accuracy, while the other two scored 0.88 and 0.86. In a subsequent experiment using 7,665 Ken Lay emails, the distribution bar graph for this experiment is illustrated in FIG. 4. The y-axis runs from 0 to only 12, indicating that the deep learning algorithm was now much more focused.

The experiments also showed that a deep learning algorithm, however well trained, will nevertheless generate an alert that a reviewer would reject for follow up. For example, the Email scoring at 0.97 was from an Enron employee in India. In part, it read: "Subsequently, I was forced upon a cheque of severance amount on 27 Aug. 2001 which I received under protest and the notice of such protest was served by me on firm in the interest of justice. I submit such a termination is illegal, bad in law and void ab-initio and accordingly when such an action was not corrected by firm, I [was] constrained to approach the Court of law." (Boldface and italics added.)

Thus, while that Email recounts a discrimination risk, the risk appears to have already become a lawsuit. A reviewing attorney might well consider this high-scoring email to be a false positive, especially if he or she determines that a lawsuit has already been filed.

A second experiment used Indico Data Systems, Inc. ("Indico") Deep Learning Algorithm to validate the previous training with MetaMind. Indico was provided with the same training data used with MetaMind and with the same test data.

The results showed that the same risky Email found using MetaMind that had text in the subject line stating, "unfair treatment at Enron," which 0.86 and 0.88 with MetaMind, was flagged Indico's model, and the same Email scored 0.89, which is comparable.

Figure 5:
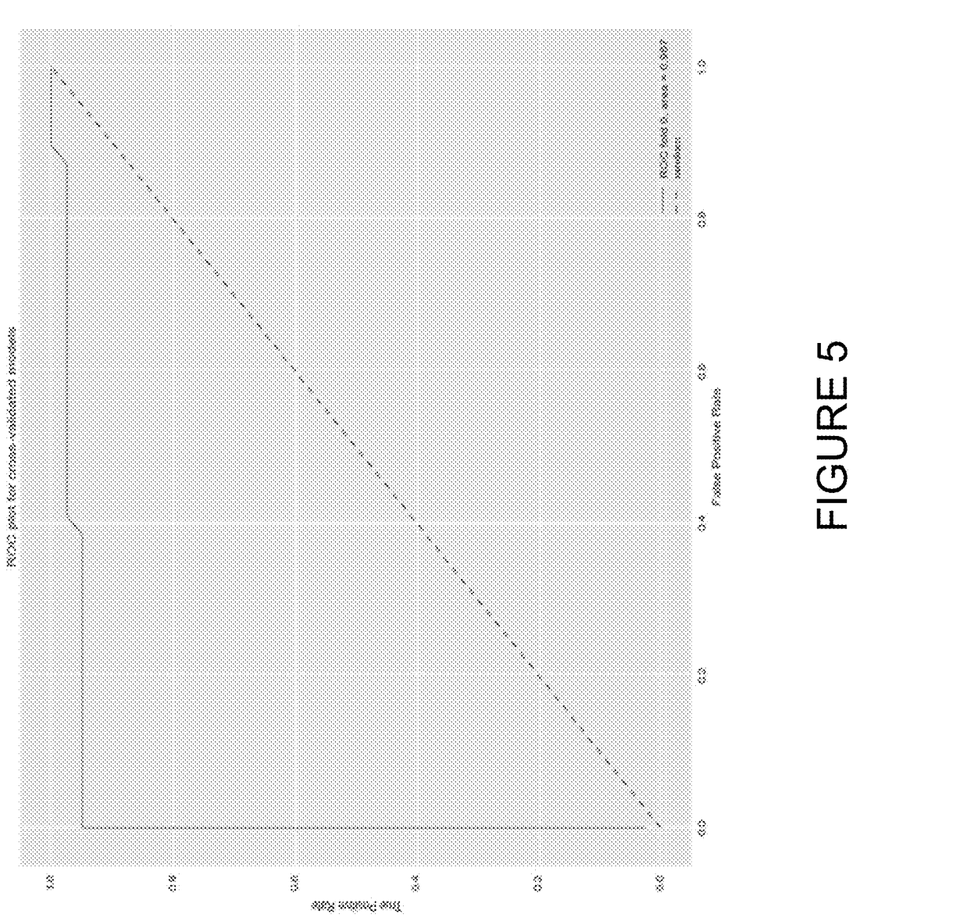
FIG. 5 is a graph of Receiver Operating Characteristic (ROC) and related Area Under the Curve (AUC).

Indico also used about 75 held-out documents in order to provide a graph of a curve showing a Receiver Operating Characteristic, illustrated in FIG. 5, which included a related indicator called the Area Under the Curve (AUC). These statistics put "true positives" on the y-axis and "false positives" on the x-axis. On both axes, the maximum score is 1.0. A strong algorithm will score high and to the left, which is what we saw.

Also since the maximum score for each axis is 1.0, the area under the ROC curve is also 1.0. According to the second provider, Indico, the AUC score was 0.967 (see the AUC score in the lower right hand corner), which means that the algorithm, as trained, is strong.

In these experiments, the early warning system, having been trained (as an example) to detect an employment discrimination risk, found one (1) email out of 7,665 emails which signaled just such a risk. Thus, the inventive concept of the system has been tested using a specific litigation category, the same training data, two different algorithms, and Enron test data, and has functioned in accordance with the inventive concept. The system, as trained, had found a needle in a haystack.

Furthermore, the early warning system would function for an authorized enterprise employee in an unobtrusive way. Enterprise personnel need not be involved in data-mining to train the Deep Learning system, and the algorithm itself would scan internal emails and would run in the background. The system would not require anyone's attention until the system had a reportable result, at a threshold the legal department could set.

At that point, the system would output an alert to a privileged list of in-house personnel, likely in-house counsel or employees under their direction and control, and they would be able to see a spreadsheet with a score in column A, the related text in column B, along with a bar chart for context, and then would be enabled to call forward the Emails of interest.

The experiments discussed above employed deep learning algorithms which are described in the academic literature as Recursive Neural Tensor Networks or as Recurrent Neural Networks (RNNs) with either Long Short-Term Memory (LSTM) or Gated Recurrent Units (GRUs). Those of skill in the arts will appreciate that use of other algorithms, including those which are now open-sourced, are contemplated.

One such variation directs the above-described system to the problem of a missed or mistaken diagnosis, which is an outcome not unlike litigation in that a missed or mistaken diagnosis is an adverse and potentially lethal situation. This problem translates into not realizing that specific tests could be ordered to confirm or reject a diagnosis which the healthcare provider has not made but which is indicated by the patient's electronic health records (EHRs), including but not limited to the provider's notes, procedures, medications, tests and test results, pathology reports, and/or diagnostic codes, all of which are collectively hereinafter referred to as Notes. Here, a healthcare provider refers to any professional licensed to provide healthcare services and may include but is not limited to physicians, nurse practitioners, nurses and chiropractors.

In this variation, a corporate (hospital) legal department may be part of the workflow but is not central to it.

Nevertheless, this variation involves using the same or substantially similar software system to identify a particular medical risk and provide early warning to healthcare providers. So stated, this variation is entirely different from recent academic papers wherein Deep Learning is trained to make diagnoses or predictions, as if in competition with healthcare providers rather than as an aid to them. See Lipton, et al., Learning to Diagnose with LSTM Recurrent Neural Networks (published as a conference paper), arXiv: 1511.03677v6 [cs.LG] 1 Mar. 2016; and Choi, et al., Doctor AI: Predicting Clinical Events via Recurrent Neural Networks, Proceedings of Machine Learning for Healthcare, arXiv:1511.05942v11 [cs.LG] 28 Sep. 2016.

Briefly stated, the system would be trained by accessing a multiplicity of previous Notes for specific diagnoses, e.g., multiple sclerosis or lupus, where a diagnosis is established by the provider using all the information available in the Notes.

The training data consisting of a sufficient number (e.g. multiple) of EHRs for each specific diagnosis would be gathered up from now-closed cases, which have been made de-identifiable in the sense of being HIPAA ("Health Insurance Portability and Accountability Act") compliant, e.g., where patient names, among other personally identifiable information, have been redacted before the data is passed to the algorithm. A Deep Learning algorithm would be trained for each specific disease by "word embeddings" such as word2vec or GloVe, both of which were previously noted.

For each diagnosis, the provider-made EHRs (in the now-closed, anonymous examples pertaining to a specific diagnosis) would constitute the training set of documents. These documents would be passed, i.e., uploaded, to the algorithm in order to train it. There would be a trained algorithm for each specific disease, as if it were a specific disease risk filter.

After training, including testing and tuning, the system would ingest provider-made EHRs (e.g., Notes) in open, pending cases, in near real-time or perhaps overnight or in batches for specific blocks of time (e.g., weekly). The system would pass the Notes as data to the algorithms, each of which would evaluate (i.e., score) the Notes, and, when an accuracy score exceeds a user-variable threshold, send its score as an alert to that patient's healthcare provider.

The alert would also include a specification of what disease or diagnosis is indicated by the physician's Notes, as scored by the algorithm, and may also include a list of symptoms, physical exam findings, tests and/or procedures the provider should consider ordering so that the physician may confirm or deny the diagnosis indicated by the algorithm. As is evident, the alert ignores whether the provider has or has not made a diagnosis.

In summary, in this variation, the system functions to provide the early warning of a specific medical risk—the risk of a missed or incorrect diagnosis—and so helps to prevent the expense and harm associated with tests, procedures, therapies or other interventions that may not be germane while also augmenting the physician's ability to avoid an adverse outcome for the patient.

While the invention herein disclosed has been described by means of specific embodiments and applications thereof, numerous modifications and variations could be made thereto by those skilled in the art without departing from the scope of the invention set forth in the claims.

What is claimed is:

1. A method of using classified text and deep learning algorithms to identify medical risk and provide early warning comprising:
    obtaining one or more training datasets for textual data corresponding to one or more risk classifications, wherein said risk classification comprises one or more specific medical diagnoses of interest;
    training one or more deep learning algorithms using said one or more training datasets;
    obtaining and indexing an internal electronic health record (EHR) of a patient;
    applying said one or more deep learning algorithms to said internal EHR to identify and report any one of said one or more specific medical diagnoses of interest;
    determining if said identified one of said one or more specific medical diagnoses of interest is a false positive or a true positive; and
    re-training said one or more deep learning algorithms if said identified one of said one or more specific medical diagnoses of interest is a false positive.

2. The method of claim 1, wherein said one or more deep learning algorithms is a framework for natural language processing of text.

3. The method of claim 1, wherein said one or more deep learning algorithms is a recurrent neural network with a multiplicity of layers and various features, including but not limited to long short-term memory or gated recurrent units.

4. The method of claim 1, wherein the one or more deep learning algorithms have been trained with different classifiers using previously classified data sourced and provided by a subject matter expert to become models for the specific medical diagnoses of interest.

5. The method of claim 1, wherein each one of said one or more deep learning algorithms has also been trained with one or more datasets unrelated to the specific medical diagnosis of interest.

6. The method of claim 1, wherein each one of said one or more deep learning algorithms scores the EHR textual data of a patient for accuracy according to one or more deep learning models for one or more specific medical diagnoses of interest and reports said scores.

7. The method of claim 6, wherein said report comprises the result of accessing one or more databases related to said one or more specific medical diagnoses to report one or more tests or clinical features that may help to evaluate the presence, absence, or likelihood of said one or more specific medical diagnoses.

8. The method of claim 1, wherein said report comprises providing the report to one or more designated physicians, research personnel or other personnel providing care to a patient.

9. The method of claim 1, wherein said report may be limited to scores which surpass one or more specified thresholds associated with each of said one or more deep learning algorithms.

10. The method of claim 1, wherein a healthcare provider or research personnel obtains one or more of said reports through a graphical user interface.

11. The method of claim 1, wherein said one or more training datasets is obtained by mining one or more Electronic Health Records for each specific medical diagnosis.

* * * * *